US008063915B2

(12) United States Patent
Champion et al.

(10) Patent No.: US 8,063,915 B2
(45) Date of Patent: Nov. 22, 2011

(54) METHOD AND APPARATUS FOR COLLECTING AND ANALYZING SURFACE WOUND DATA

(75) Inventors: Howard Champion, Annapolis, MD (US); Paul Sherman, Seattle, WA (US); Mary M. Lawnick, Olney, MD (US); Paul M. Cashman, North Reading, MA (US); Harald Scheirich, Washington, DC (US); Timothy Patrick Kelliher, Scotia, NY (US)

(73) Assignee: Simquest LLC, Silver Spring, MD (US)

( * ) Notice: Subject to any disclaimer, the term of this patent is extended or adjusted under 35 U.S.C. 154(b) by 846 days.

(21) Appl. No.: 11/756,908

(22) Filed: Jun. 1, 2007

(65) Prior Publication Data

US 2008/0098333 A1 Apr. 24, 2008

Related U.S. Application Data

(60) Provisional application No. 60/809,853, filed on Jun. 1, 2006.

(51) Int. Cl.
*G09G 5/00* (2006.01)

(52) U.S. Cl. ........ 345/619; 345/629; 345/630; 345/632; 345/633

(58) Field of Classification Search .................. None
See application file for complete search history.

(56) References Cited

U.S. PATENT DOCUMENTS

| 5,151,856 | A | 9/1992 | Halmann |
| 5,999,840 | A | 12/1999 | Grimson |
| 6,413,212 | B1 * | 7/2002 | Raab ............................. 600/300 |
| 6,430,430 | B1 | 8/2002 | Gosche |
| 6,669,635 | B2 | 12/2003 | Kessman |
| 6,701,174 | B1 | 3/2004 | Krause |

(Continued)

FOREIGN PATENT DOCUMENTS

WO 96/19774 A1 6/1996

OTHER PUBLICATIONS

Notification of transmittal of International Search Report and Written Opinion; International Search Report and Written Opinion of the International Searching Authority issued in PCT/US2007/12926, Sep. 30, 2008, 13 pages.

(Continued)

*Primary Examiner* — Kee M Tung
*Assistant Examiner* — Jwalant Amin
(74) *Attorney, Agent, or Firm* — Pillsbury Winthrop Shaw Pittman LLP

(57) ABSTRACT

A 3D surface wound, injury, and personal protective equipment (PPE) data entry system provides an easily usable graphical user interface through which an examiner can objectively record data relating to surface wounds and injuries sustained by a subject human, as well as PPE used when the wounds/injuries were sustained. The system includes a 3D human model onto which the examiner draws the surface wound(s) and/or damage to the PPE. The subject human's record is stored in a database of similar records. The database records comprise quantifiable, objective data that is easily compared and analyzed. An analysis tool can aggregate a selected population of human subjects within the database to create wound density information that can be statistically analyzed and/or displayed on a standard 3D human model. Such objective wound density information may facilitate improved medical and/or tactical training, and improved PPE design.

17 Claims, 5 Drawing Sheets

U.S. PATENT DOCUMENTS

| | | |
|---|---|---|
| 6,950,689 B1 | 9/2005 | Willis |
| 6,968,224 B2 | 11/2005 | Kessman |
| 2004/0059199 A1 | 3/2004 | Thomas |
| 2005/0131738 A1 | 6/2005 | Morris |

OTHER PUBLICATIONS

Digital Innovation, Inc., Reliable Medical Registry Solutions, Information product sheets from website: www.dicorp.com/Products_CollectorFeatures.html, May 29, 2007, 3 pages.

BurnCase 3D, 3D Burn Documentation for Professionals, search result from website: www.burncase.at/home.htm, May 30, 2007, 3 pages, Feb. 2003.

BurnCase 3D, 3D Burn Documentation for Professionals, search result from website: www.burncase.at/index.php, Jun. 5, 2007, 24 pages, Feb. 2003.

Ogunyemi et al., "Methods for reasoning from geometry about anatomic structures injured by penetrating trauma", J. Biomed. Informatics, Acad. Press, NY, vol. 39, No. 4, pp. 389-400 (2005).

Holzman, "Computer-human interface solutions for emergency medical care", Interactions, vol. 6, No. 3, pp. 13-24 (1999).

Benoit et al., "Direct Physician Entry of Injury information and automated coding via a graphical user interface", Proceedign. Symposium on Computer Applications in Medicalcare, pp. 787-788 (1993).

Dirnberger et al., "BurnCase 3D Core Benutzerhandbuch", Upper Austrian Research GmbH, pp. 1-87 (2004).

Supplementary European Search Report dated May 10, 2010 of EP Appl. No. 07809275.6 (11 pages).

\* cited by examiner

METHOD AND APPARATUS FOR COLLECTING AND ANALYZING SURFACE WOUND DATA

This application claims the benefit of priority of provisional application Ser. No. 60/809,853, filed Jun. 1, 2006, the entire contents of which is incorporated by reference herein.

STATEMENT REGARDING FEDERALLY SPONSORED RESEARCH AND DEVELOPMENT

The U.S. Government has a paid-up license in this invention and the right in limited circumstances to require the patent owner to license others on reasonable terms as provided for by the terms of TSWG Contract No. N41756-06-C5518, titled "Clinical Specification of Next Generation Body Armor," awarded by the Technical Support Working Group (TSWG) of the U.S. Department of Defense.

BACKGROUND OF THE INVENTION

1. Field of the Invention

The present invention relates to the collection and analysis of data relating to surface wounds suffered by a population of humans.

2. Description of Related Art

When humans (e.g., military and/or civilian) sustain surface wounds (fatal or non-fatal), it is common for a medical practitioner or examiner to record data associated with the surface wounds and injuries. The term "wound" refers to the tearing of the skin by a bullet, fragment, etc. The term "injury" refers to the trauma to the internal organ. A fragment might come in through the front of the chest and exit the person's back, causing two wounds. On the way through it might hit the right lung and aorta, causing two injuries. The examiner typically records such surface wound and internal injury data as subjective notes. The examiner may indicate the location, size, and shape of the surface wound(s) on 2D anterior and posterior human outlines on a sheet of paper.

There is a need to statistically analyze such wound data and associated injury data to identify trends/patterns over a large population of wound victims. Unfortunately, it is difficult or impossible to objectively/quantifiably compare conventional wound/injury data due to its subjective language and non-quantified description of the location of surface wounds and injuries. Consequently, individuals wishing to analyze such wound/injury data must rely on qualitative analysis. There remains a need for a method and apparatus for objectively collecting and analyzing surface wound data.

BRIEF SUMMARY OF THE INVENTION

Accordingly, one or more embodiments of the present invention provides a method and apparatus for objectively/quantifiably recording 3D data indicating the location of human surface wounds by drawing surface wounds onto a virtual, parameterized 3D human model. The objective data may also include data relating to injuries associated with the surface wounds, as well as data relating to personal protective equipment (PPE) used by the human when wounded. Such objective data may be added to a database containing additional records for additional surface wounds/injuries/PPEs and/or additional subject humans. The database can then be statistically analyzed to objectively identify trends, patterns, wound densities, etc. for a population of subject humans. The records can be filtered based on a variety of criteria in the records to analyze focused subsets of the records. The analysis may be used for various purposes (e.g., improve medical training for common surface wounds; improve PPE such as body armor for body areas that are commonly wounded; improve PPE design for parts of PPEs that commonly fail, especially where failure results in more severe wounds/injuries; improve tactical training for military personnel to better protect commonly wounded areas of the body, etc.).

Another aspect of one or more embodiments of the present invention provides a method of collecting wound information. The method includes recording at least one surface wound subrecord into a first electronic record for a first subject human. Recording each of the at least one surface wound subrecords comprises drawing location information of a surface wound sustained by the first subject human onto computer-generated skin of a computer-generated 3D human model, and recording that location information to the associated surface wound subrecord. The method also includes recording at least one injury subrecord into the first electronic record, wherein recording each of the at least one injury subrecords comprises recording information concerning an injury sustained by the first subject human. The method also includes recording in the first electronic record a relationship between at least one of the surface wound subrecords and at least one of the injury subrecords.

According to a further aspect of one or more of these embodiments, the method also includes, prior to drawing the location information, recording into the first electronic record at least one body characteristic for the first subject human. At least one characteristic of the 3D human model is based on the recorded at least one body characteristic, and the at least one body characteristic comprises at least one of height, weight, gender, and body type.

According to a further aspect of one or more of these embodiments, the method also includes recording into at least one of the surface wound subrecords tactical data relating to a circumstance under which the associated surface wound was sustained.

According to a further aspect of one or more of these embodiments, the location information includes 3D vector information of an entry or exit direction associated with the surface wound.

According to a further aspect of one or more of these embodiments, the 3D human model has internal anatomical landmarks, and drawing the location information includes selectively changing a transparency of the skin to facilitate location of the surface wound relative to at least one of the internal landmarks. The internal landmarks may include skeletal landmarks and/or internal organ landmarks.

According to a further aspect of one or more of these embodiments, a database includes the first electronic record and a plurality of additional electronic records for a plurality of additional subject humans. Each of said plurality of additional records includes at least one associated surface wound subrecord and at least one injury subrecord. As explained below, statistical analysis may be conducted on the entire population of records, or a filtered subset of the records.

According to a further aspect of one or more of these embodiments, the method also includes correlating the first electronic database record to a 3D medical image of the first human. The method may include displaying a 3D medical image of the first human and the drawn wound information in a superimposed view. The method may include analyzing an injury shown in the 3D medical image in view of the drawn location information. The method may include using a superimposed 3D medical image of the first human to locate the surface wound on the model.

According to a further aspect of one or more of these embodiments, recording each of the at least one surface wound subrecords comprises entering additional information about the drawn surface wound, including at least one of: a severity of the surface wound, a wound type for the surface wound, wound entry information, wound exit information, wound path information, wound depth, amputation category of the surface wound, tourniquet status, notes relating to the surface wound, an identification of the first human, time of injury causing the surface wound, date of injury causing the surface wound, gender of the first human, height of the first human, weight of the first human, and body type of the first human.

According to a further aspect of one or more of these embodiments, the method also includes recording at least one personal protective equipment subrecord into the first electronic record, each of the at least one personal protective equipment subrecords comprising information relating to personal protective equipment used by the first subject human when the first subject human was wounded. Recording each of the at least one personal protective equipment subrecords includes drawing damage location information relating to damage sustained by the personal protective equipment onto a computer-generated representation of the personal protective equipment. The method may also include recording in the first electronic record a relationship between at least one of the surface wound subrecords and at least one of the personal protective equipment subrecords.

Another aspect of one or more embodiments of the present invention provides a method of collecting wound information. The method includes drawing location information of a surface wound of a subject human onto computer-generated skin of a computer-generated 3D human model, the location information including 3D vector information of an entry or exit direction associated with the surface wound. The method also includes recording the location information into an electronic record of a database.

Another aspect of one or more embodiments of the present invention provides a surface wound data entry system for carrying out the above-described method.

Another aspect of one or more embodiments of the present invention provides a method of analyzing surface wound information stored in a database, the database comprising a plurality of electronic database records, each record of which comprises at least one surface wound subrecord, each surface wound subrecord comprising location information for a surface wound sustained by an associated subject human. The method includes statistically analyzing the electronic database records.

According to a further aspect of one or more of these embodiments, analysis may be done on a filtered subset of the total record population. Filtering may be done based on at least one selected criterion within the records. Filtering may include drawing a surface region onto computer-generated skin of a computer-generated 3D human model, filtering the electronic database records to identify a subset of records that contain surface wounds sustained in the drawn surface region, and statistically analyzing the subset of the electronic database records.

According to a further aspect of one or more of these embodiments, the statistical analysis comprises aggregating the records to identify wound density as a function of surface location over a plurality of subject humans.

According to a further aspect of one or more of these embodiments, filtering criterion includes at least one of: injuries occurring before or after selected times and/or dates; injuries occurring during selected time and/or date ranges; AIS code of injuries/wounds; injury/wound severity; information associated with injuries that caused the wound(s); injury mechanism; geographic location where injury was incurred; surface wound type; location of the surface wound on the subject human; subject human information; an ISS code for the subject human; and presence and/or type of personal protective equipment used.

According to a further aspect of one or more of these embodiments, each surface wound within a subrecord is associated with injury information relating to a severity of an injury associated with the surface wound, and the wound density is identified as a function of injury severity.

According to a further aspect of one or more of these embodiments, the method further includes displaying the wound density on a computer-generated 3D human model; and adding a 3D model of personal protective equipment to the computer-generated 3D human model to display wound density relative to personal protective equipment location.

According to a further aspect of one or more of these embodiments, a plurality of the database records include at least one personal protective equipment subrecord, each personal protective equipment subrecord of which contains information relating to personal protective equipment utilized by the associated subject human when the subject human was wounded. Each personal protective equipment subrecord includes location information relating to damage sustained by the personal protective equipment when the subject human was wounded. The statistical analysis comprises aggregating a plurality of the records to identify personal protective equipment damage density as a function of surface location on the personal protective equipment. Each personal protective equipment subrecord may include severity of damage information, and the damage density may be identified as a function of damage severity.

Another aspect of one or more embodiments of the present invention provides a method of recording damage to personal protective equipment. The method includes recording at least one electronic personal protective equipment record for personal protective equipment that was damaged. Recording each of the at least one personal protective equipment records includes drawing damage location information relating to the damage sustained by the personal protective equipment onto a computer-generated representation of the personal protective equipment, and recording the location information into the associated personal protective equipment record.

According to a further aspect of one or more of these embodiments, the method also includes, prior to drawing the location information, recording into the associated electronic record at least one characteristic of the personal protective equipment, wherein at least one characteristic of the computer-generated representation of the personal protective equipment is based on the recorded at least one characteristic of the personal protective equipment.

According to a further aspect of one or more of these embodiments, the method also includes recording into at least one of the personal protective equipment records tactical data relating to a circumstance under which the associated damage was sustained.

According to a further aspect of one or more of these embodiments, the location information includes 3D vector information of an entry or exit direction of an object that caused the damage.

According to a further aspect of one or more of these embodiments, recording each of the at least one personal protective equipment records further comprises recording a severity of the damage.

Another aspect of one or more embodiments of the present invention provides a personal protective equipment damage recording system for carrying out the above-described method.

Another aspect of one or more embodiments of the present invention provides a method of analyzing a plurality of personal protective equipment records stored in an electronic database, each record of which comprises location information relating to damage sustained by personal protective equipment. The method includes statistically analyzing the electronic database records.

Statistically analyzing the electronic database records may include analyzing a subset of the records, the subset being based on at least one selected criterion within the records.

Statistically analyzing the electronic database records may include drawing a surface region onto a computer-generated representation of the personal protective equipment, filtering the electronic database records to identify a subset of records that contain damage sustained in the drawn surface region, and statistically analyzing the subset of the electronic database records.

The statistical analysis may include aggregating the records to identify damage density as a function of surface location over a plurality of samples of personal protective equipment.

According to a further aspect of one or more of these embodiments, within a plurality of the records, the damage is associated with injury information relating to a severity of an injury associated with the damage, and the damage density is identified as a function of injury severity.

According to a further aspect of one or more of these embodiments, the method includes improving personal protective equipment to better protect areas that the analysis identifies as having a high damage density.

According to a further aspect of one or more of these embodiments, each personal protective equipment record further comprises damage severity information associated with the respective location information. The damage density is identified as a function of damage severity.

Additional and/or alternative advantages and salient features of the invention will become apparent from the following detailed description, which, taken in conjunction with the annexed drawings, disclose preferred embodiments of the invention.

BRIEF DESCRIPTION OF THE DRAWINGS

Referring now to the drawings which form a part of this original disclosure.

DETAILED DESCRIPTION OF EMBODIMENTS OF THE INVENTION

Figure 1:
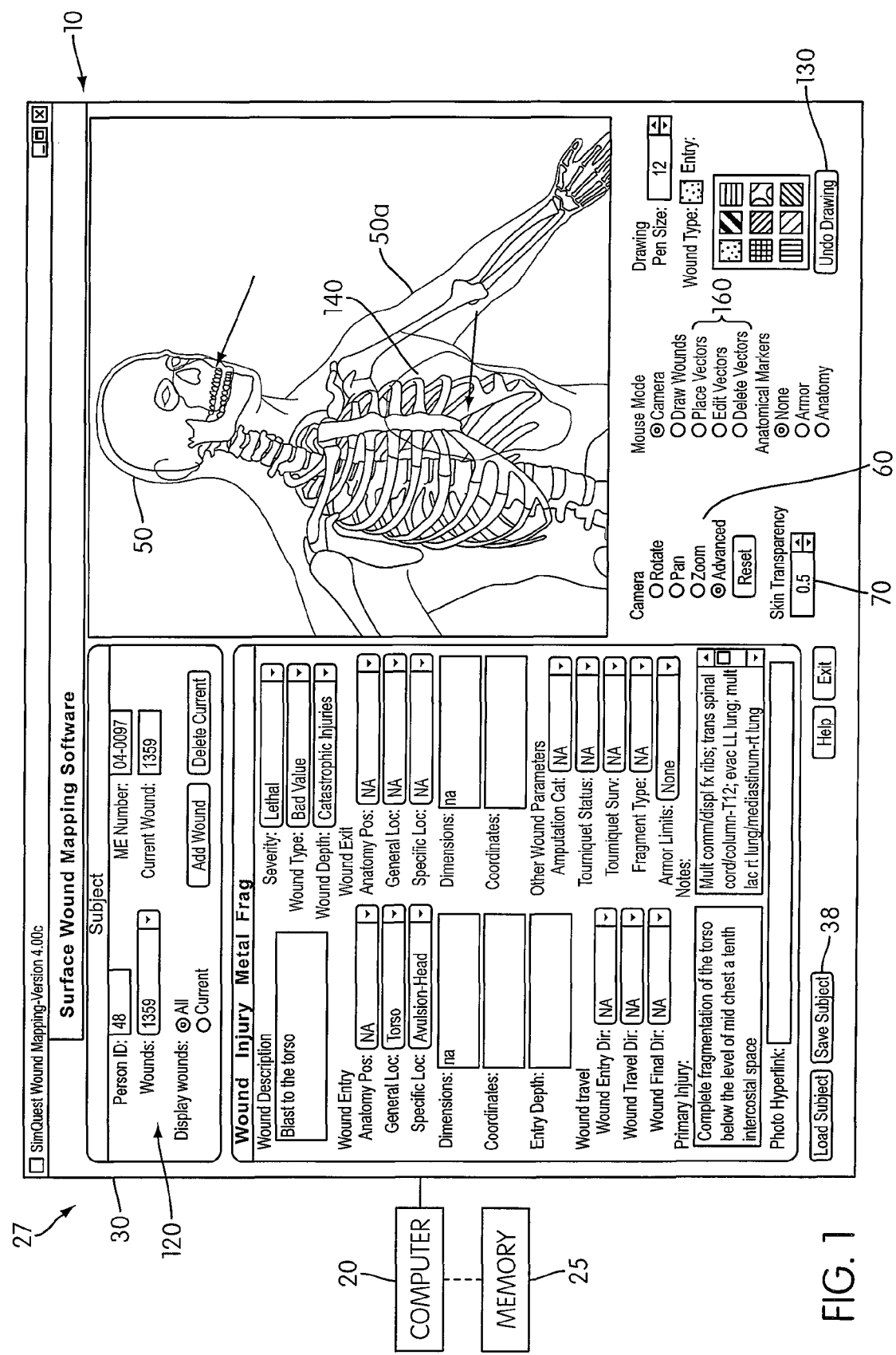
FIGS. 1-3 are screenshots illustrating the use of a surface wound data entry system according to an embodiment of the present invention.
Figure 2:
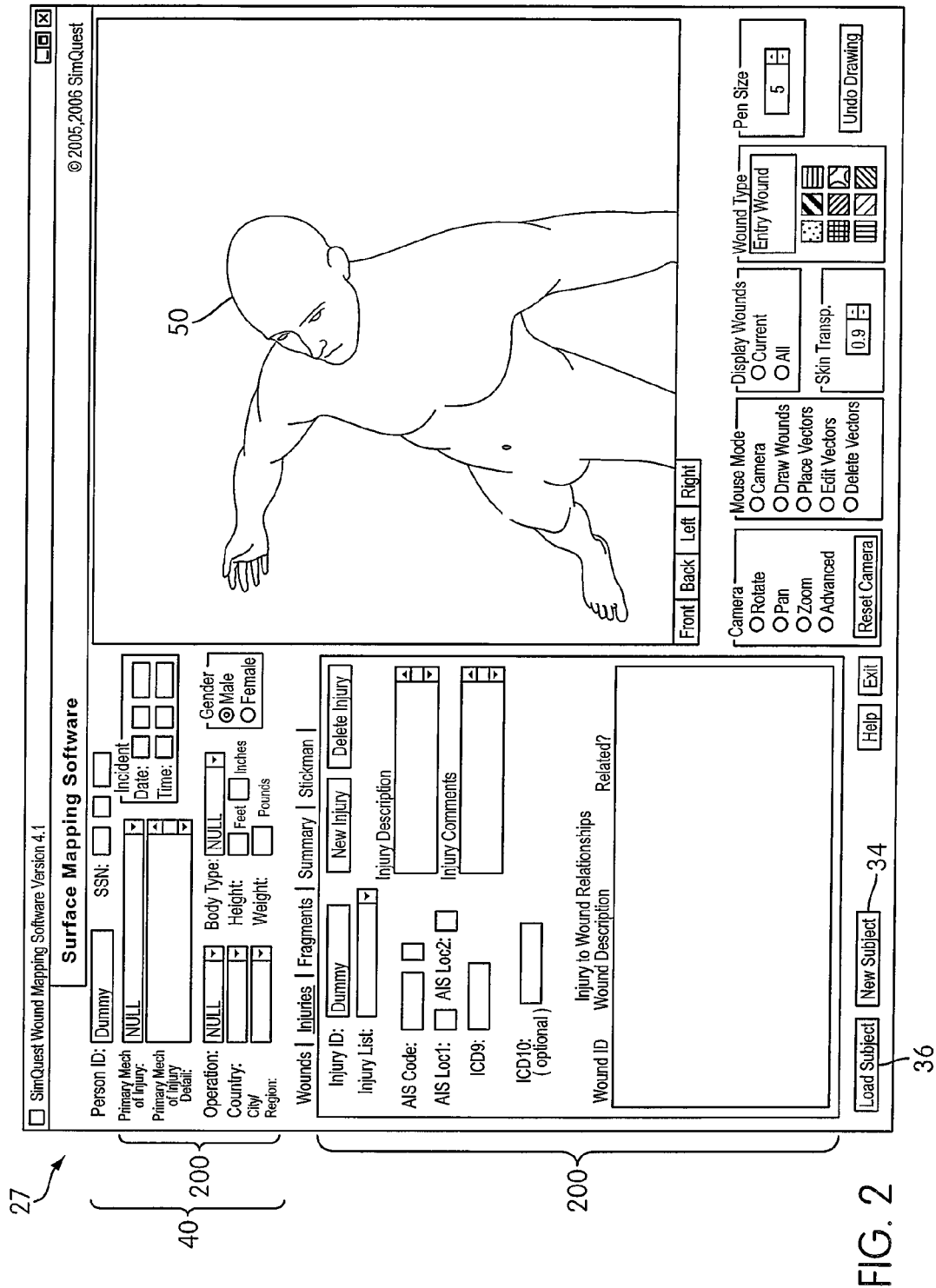
Figure 3:
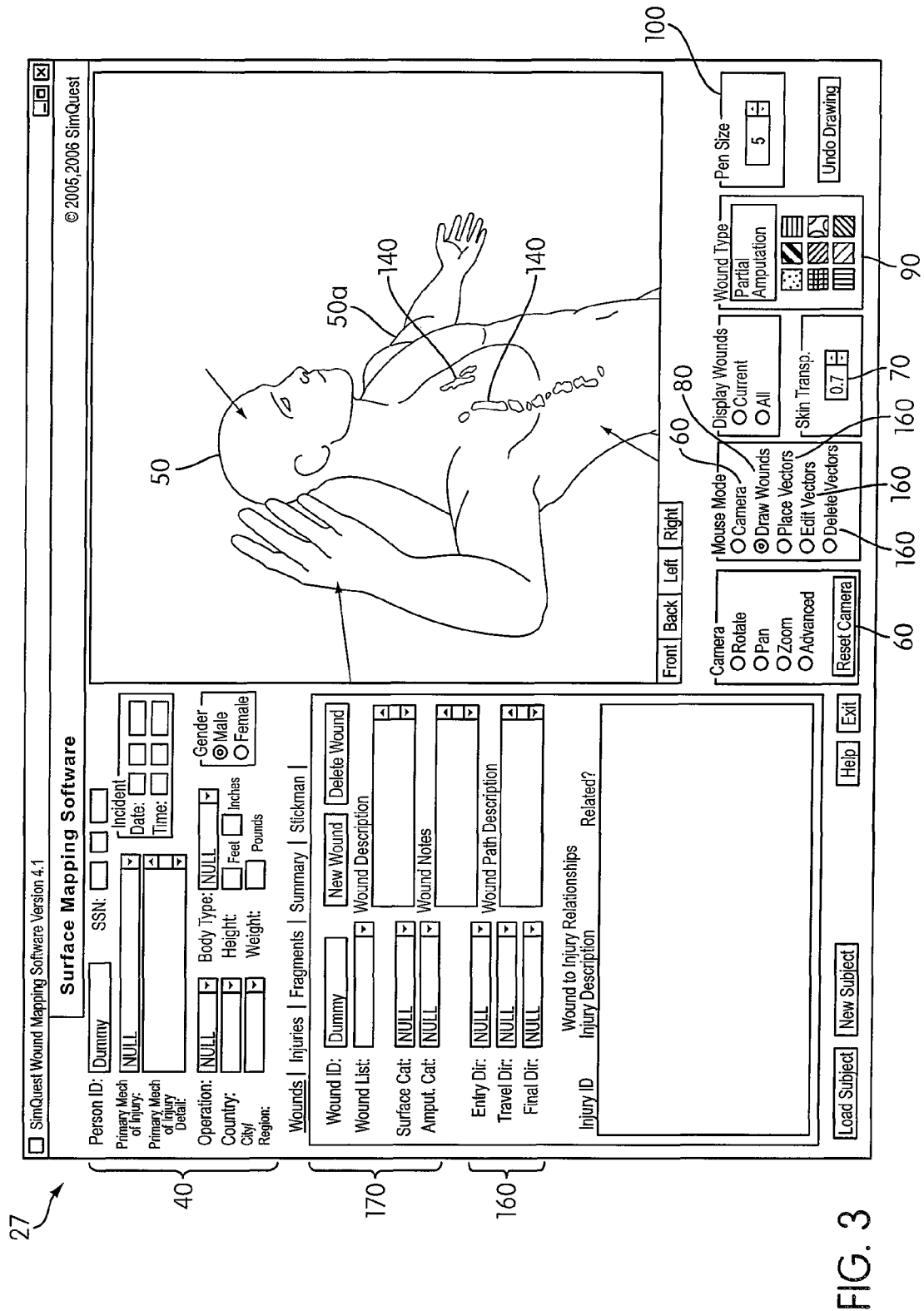

FIGS. 1-3 illustrate screenshots of a surface wound data entry system 10 according to an embodiment of the present invention. As shown in FIG. 1, the illustrated system 10 is incorporated into a computer program that is run on a computer 20 with a memory device 25 and a display 30 (e.g., computer monitor, TV, etc.). However, according to an alternative embodiment of the present invention, the system 10 is incorporated into a stand-alone apparatus. While the illustrated memory device 25 is part of the computer 20, the memory device 25 may alternatively be separate from the computer 20 and even disposed in a different geographical location from the computer 20 (e.g., a central data repository). The memory device 25, itself, may comprise a plurality of separately located memories.

As shown in FIGS. 1-3, the system 10 includes a simple, easily usable graphical user interface (GUI) 27 that enables a medical examiner or practitioner to quickly, accurately, and objectively record a description of surface wounds of subject human(s) (live or dead) at the point of care/access. The resulting record is in a well-defined, extensible format that can be easily objectively analyzed.

As shown in FIG. 2, the system 10 includes a "New Subject" button 34 that enables an examiner to start a new record. When the "New Subject" button 34 is actuated, the system 10 creates a corresponding record in the memory device 25 (e.g., hard drive, CD, flash memory, networked memory, etc.). The system 10 stores all input information about the subject human in the corresponding record. Input information may be recorded to the record as soon as it is input by the examiner, or when the examiner actuates a "Save subject" button 38. The system 10 also includes a "Load Subject" button 36 that enables the examiner to alternatively retrieve an existing record for modification and/or augmentation.

The system 10 includes a plurality of data entry fields in various forms (e.g., text boxes, drop-down menus, check boxes, etc.). As shown in FIG. 2, a plurality of fields 40 are provided for general information about the subject human (e.g., Person ID (e.g., patient number), Social Security Number, body type, height, weight, gender, etc.). The system 10 records the general information to the record in the memory device 25.

As described in greater detail below, the system 10 includes various features to facilitate accurate and precise recordation of the location of surface wounds sustained by the subject human.

As shown in FIG. 1, the system 10 includes a surface wound subrecord tool 120 that enables the examiner to create, modify, view, and delete a plurality of subrecords for a plurality of respective surface wounds within a record for a particular subject human. The system 10 (or examiner) assigns each new surface wound subrecord a number (or other reference). The tool 120 may enable the examiner to selectively view one, a select plurality, or all of the surface wound subrecords in the record.

As shown in FIGS. 1 and 3, the system 10 facilitates identification of the three dimensional location of a surface wound by providing a virtual 3D parameterized human model 50 onto which the surface wound is drawn by the examiner. The system 10 may use the information entered into the general information fields 40 (e.g., body type, height, weight, and/or gender) to modify the size and/or shape of the model 50 to more accurately and/or precisely represent the subject human.

As shown in FIGS. 1 and 2, the system 10 includes a pan/zoom/tilt (PZT) viewing/camera tool 60 that enables the examiner to modify the view of the model 50 in the GUI 27. For example, the viewing/camera tool 60 enables an examiner to: rotate the model 50 about one, two, and or three orthogonal coordinate axes; zoom in and out; and pan up, down, left, and right. The viewing/camera tool 60 also includes an "Advanced" camera mode that provides a combination of mouse-based pan/zoom/tilt functions, as is common in the conventional 3) computer graphics field. The viewing/camera tool 60 also includes a "Reset Camera" button that resets the view to an anterior view. Additionally, the viewing/camera tool 60 includes "Front" (anterior), "Back" (posterior), "Left" (left lateral view), and "Right" (right lateral view) buttons to snap the model 50 to the named view. The viewing/camera tool 60 enables the examiner to orient the model 50 so as to best display an area of the model 50 in which the subject human incurred a surface wound, thereby facilitating more accurate drawing of the subject human's surface wound on the model 50. Typically, the examiner will orient the model 50 such that the surface of interest is perpendicular to a viewing direction (i.e., the skin surface 50a is generally parallel to a surface of the display 30).

As shown in FIGS. 1 and 2, the model 50 includes a contoured skin surface 50a (shown solidly in FIG. 2) and internal landmarks 50b (shown in FIG. 1) to help the examiner precisely identify locations on the model 50. The contoured skin surface 50a includes external anatomical landmarks (e.g., bulges in the skin contour to identify underlying muscles, boney protuberances, etc.; standard anatomical surgical landmarks, etc.). The illustrated internal landmarks 50b comprise skeletal landmarks, but may additionally and/or alternatively comprise other internal landmarks such as internal organs, veins, blood vessels, etc. without deviating from the scope of the present invention. The internal and external landmarks and skin contours help an examiner to accurately and precisely identify a desired skin surface location on the model 50 that corresponds to a surface wound on the subject human.

As shown in FIGS. 1 and 2, the system 10 includes a skin transparency control 70 that enables an examiner to modify a transparency of the skin 50a of the model 50 to make the internal landmarks 50b more visible (FIG. 1) or less visible (FIG. 2). In the illustrated embodiment, the control 70 is variable between 0.1, which represents maximum skin transparency, and 1.0, which corresponds to opaque skin.

The model 50 may be articulatable to enable the examiner to position the model 50 to reflect the subject human's pose when wound-causing injury was sustained or to provide a better view of any desired skin surface 50a area. For example, as shown in FIG. 3, the right arm of the model 50 is articulated into a raised position. As another example, if a wound-causing injury was sustained while the subject human was driving a vehicle, the model 50 may be articulated into a sitting position that corresponds to a position of a seated driver.

As shown in FIG. 3, the system 10 includes a wound drawing feature 80 that enables the examiner to accurately and precisely draw surface wound details of the subject human onto the model 50. The system 10 enables the examiner to select different pen colors 90 for drawing different types of surface wounds onto the model 50 (e.g., complete amputation; partial amputation; avulsion (skin/soft tissue/external wounds); blunt force; catastrophic; gaping laceration; multiple; other; penetrating entrance (for a wound entrance of a fragment or other penetrating wound); penetrating exit (for a wound exit for fragment or other penetrating wounds; thermal; unknown; etc.)). The system 10 also enables the examiner to select a pen size 100 that is appropriate for the surface wound to be drawn.

As shown in FIGS. 1 and 3, after appropriately setting the PZT view of the model 50, the skin transparency of the model 50, and the pen color and size, and selecting/creating a surface wound subrecord, the system 10 enables the examiner to use a mouse to draw a surface wound 140 of the subject human onto the skin surface 50a of the model 50. The drawn wound 140 may comprise a single dot, a line, or a wound perimeter that is then filled in by the examiner. The system 10 includes an "Undo Drawing" button 130 that erases the most recently drawn surface wound 140. The system 10 records location information associated with the drawn surface wound 140 to the memory device 25. Such location information may include size, shape, location, etc. of the drawn surface wound 140. The model 50 preferably includes an embedded coordinate frame system to precisely and accurately define the location, size, shape, etc. of the drawn surface wound 140. The coordinate system may be parameterized to vary based on the subject human's body characteristics while maintaining a standardized reference coordinate system that can be compared across body types when the records are subsequently analyzed, as discussed in detail below.

In the illustrated embodiment, the examiner draws the surface wound 140 using a mouse. However, various other methods of drawing the surface wound 140 onto the model 50 may be alternatively/additionally be used to draw the surface wound 140 without deviating from the scope of the present invention (e.g., drawing the surface wound 140 onto a stylus-based system such as is found on personal digital assistants (PDAs) that replaces the display 30; providing a coordinate system on the model 50 to enable the examiner to numerically enter coordinates corresponding to the location, size, and shape of the surface wound on the subject human, etc.).

As shown in FIG. 3, the system 10 also includes a wound vector tool 160 that enables an examiner to add geometrically-based wound vector information to the surface wound subrecord. The wound vector tool 160 enables the examiner to draw, edit, and delete 3D vectors associated with the wound's entry or exit direction (e.g., coordinate-based angle of incidence).

The system 10 includes various fields 170 for recording additional information relating to the selected surface wound subrecord. The fields 170 may include one or more of: a severity of the surface wound, a wound type for the surface wound, wound depth, amputation category of the surface wound, entry direction, travel direction, final direction, wound path description, tourniquet status, notes relating to the surface wound, wound description, AIS code for the surface wound, etc. The fields may also include various tactical data relating to the incident that resulted in the wounds (e.g., time and/or date of incident, location of incident (e.g., country, region, town, GPS coordinates, etc.), whether the subject human was in a vehicle or not (dismounted), distance to the nearest vehicle in convoy or person in patrol, type of incident (e.g., improvised explosive device (IED) and subtype of IED, size of explosive, type of explosive, sniper fire, EFP, etc.), primary wounding mechanism, information about the munition (e.g., weight, material, type of casing, standoff, etc.) or projectile (e.g. caliber, fragment size, speed of impact, etc.), etc. If the subject human was in a vehicle, additional fields may prompt the examiner to enter further details such as the type of vehicle, the subject human's position in the vehicle (e.g., driver, gunner, etc.), the speed of vehicle when the incident occurred, road surface type when the incident occurred, post-incident description of the damage to the vehicle, etc. The fields 170 may take any objective or subjective form (e.g., drop-down menus, text boxes, etc.).

The system 10 also includes an injury subrecord entry tool 200 to enable the examiner to create, modify, view, and delete a plurality of injury subrecords for a plurality of respective injuries associated with one or more of the wound subrecords within a record for a particular subject human. The system 10 (or examiner) assigns each new injury subrecord a number (or other descriptor). The tool 200 may enable the examiner to record such injury information as: any of the fields described above with respect to surface wound information, type of injury, text-based description of the injury, injury comments, AIS (the Abbreviated Injury Scale of the Association for the Advancement of Automotive Medicine) code for the injury, AIS Loc1 and AIS Loc2 (codes based on body location), ICD10 (International Classification of Diseases and Related Health Problems), and relationship(s) between the injury and one or more surface wound subrecords.

To relate an injury subrecord to a wound subrecord, the examiner selects a wound subrecord from list of existing wound subrecords. The examiner records the relationship and also records a certainty to which the examiner thinks the injury is related to the wound. The process may be repeated to relate additional wound subrecords to the injury subrecord.

The examiner preferably enters surface wound and injury data into the system 10 when the examiner has actual access to the subject human (whether living or deceased). Entry of information during contemporaneous access to the subject human facilitates accurate recordation of wound/injury information and more accurate drawing of the surface wound(s) 140.

The system 10 may also enable an actual 3D medical image (e.g., MRI, CT scan, etc.) of the subject human to be added to the record. The system 10 may superimpose the 3D image onto the model 50 to facilitate cross-reference of actual image data relating to surface wounds and internal injuries to the drawn surface wounds 140. The superimposition may improve analysis of the actual imaged internal injuries based on recorded wound subrecords (e.g., wound vectors, location, size, etc.). Conversely, the actual imaged internal injuries may improve recordation and/or analysis of the related wound subrecord(s).

Figure 4:
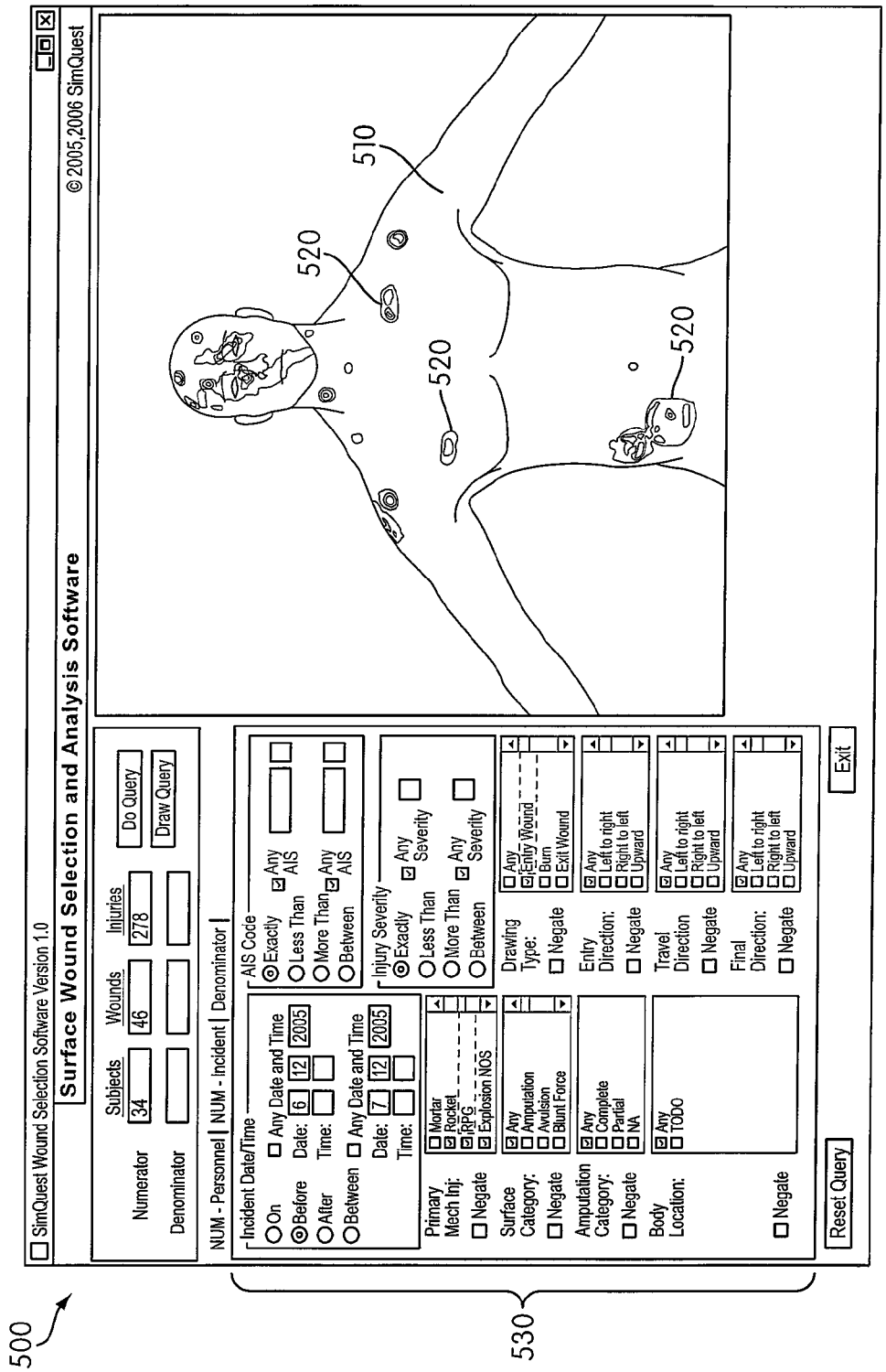
FIG. 4 is a screenshot illustrating the use of a surface wound analysis system according to an embodiment of the present invention.

FIG. 4 is a screenshot illustrating a surface wound analysis system 500 according to an embodiment of the present invention. The illustrated system 500 is incorporated into a computer program that is run on the computer 20 and displayed on the display 30. However, according to an alternative embodiment of the present invention, the system 500 may be incorporated into a stand-alone apparatus. The system 500 analyzes a plurality of surface wound data records obtained via the above-described system 10 and/or one or more additional data entry systems. The plurality of records define a database of records that may be centrally or separately stored in one or more memory devices.

The system 500 includes tools to perform various statistical and graphical analyses of the database information. The objective, quantified information in each record facilitates the objective computer-driven analysis of the records. The analysis may account for differences in morphology and body pose of the various subject humans. The system 500 may reduce or eliminate individual variability due to morphology, body pose, and/or body characteristics to standardize each record, thereby standardizing the results of analysis performed on the records.

As illustrated in FIG. 4, the system 500 may aggregate the records and graphically display the aggregated information on a computer-generated standard parameterized 3D human model 510 as wound density information 520 that varies as a function of skin surface location. Records and/or surface wound subrecords may be included or excluded from the aggregated information using various filtering tools 530. The tools 530 may filter surface wound subrecords into or out of the aggregated information based on such information as: injuries occurring before or after selected times and/or dates; injuries occurring during selected time and/or date ranges; AIS code of injuries/wounds; injury/wound severity; information associated with injuries that caused the wound(s); injury mechanism; geographic location where injury was incurred; surface wound type; location of the surface wound on the subject human; subject human information; an ISS code for the subject human; presence and/or type of personal protective equipment used; circumstances under which the wound, injury, or damage occurred; and/or any other information collected in the various subrecords. The drawn surface wounds 140 and entry and exit wound vectors may be selectively included or excluded from the displayed aggregated information. Records and/or wound subrecords may be specifically included or excluded by reference number to analyze select populations of the subject humans. Additional/alternative criteria may also be used.

For example, one report may aggregate only records for subject humans who were driving a vehicle when the incident occurred. The model 510 may be articulated into the position of a seated driver to better illustrate the wound density incurred by a population of drivers. The report may be further filtered to include only those wounds and/or injuries that resulted from a particular type of incident (e.g., only projectiles, only explosions, etc.). Such information may be used to improve vehicle design to better protect against more common and/or more severe types of wounds, as highlighted by the wound/injury/etc. density illustrations.

A plurality of such filtered aggregations may be simultaneously shown. For example, aggregations may be prepared for each seating location in a particular vehicle. Models 510 may be articulated into the corresponding positions and locations relative to each other with the corresponding aggregated density information shown on each model 510. Such an aggregation of aggregations may help vehicle and/or vehicle armor designers to consider simultaneously how various improvements to the vehicle may reduce injuries to individuals sitting in different positions in the vehicle. A 3D graphical representation of the particular vehicle may be overlaid onto the models 510. The vehicle representation preferably has a variable transparency.

As shown in FIG. 4, the system 500 may display wound density by overlaying all selected drawn surface wounds 140 within the selected surface wound subrecords. Additionally/alternatively, the system 500 may illustrate wound density by varying colors (or other indicia) on the skin contour of the model 510 as a function of the surface wound density. For example, redder areas may be used to indicate higher wound density, while greener areas may be used to indicate low wound density. The system 500 may also display the aggregated information as a weighted function of associated injury severity such that more wounds associated with more severe injury subrecords are given greater weight in the wound density analysis.

The system 500 may enable 3D models of PPE to be graphically overlaid onto the model 510 and graphical wound density display. PPE includes such equipment as body armor (e.g., helmets (CVC, LWH (light weight helmet), etc.), vests (e.g., IBA (interceptor body armor)), plates (e.g., SAPI, ESPAI), groin extension, nape extension, goggles, etc.), fire retardants (e.g., NOMEX™ Fire Resistant suit (e.g., gloves, head protection, shirt, etc.)), and/or chemical protective gear (e.g., gloves, breathing mask, etc.). Illustrations of such PPE may help PPE designers to design or modify PPE to better protect humans from common or severe wounds (e.g., strengthen or provide PPE where high wound densities are identified). For example, the wound trajectory vectors may help PPE designers improve PPE to specifically protect against objects/projectiles (e.g., fragments, bullets) that enter the subject humans via common and/or severely injurious entry vectors. The geometrically-based 3D vectors provide more precise information to designers than was previously available via conventional qualitative descriptions of wound trajectories. As explained below, recordation of specific personal protective equipment used when a subject human was injured may further improve the design of PPE.

The system 500 may help medical training personnel to focus medical training on the most common and/or most common, severe types of wounds that will be encountered in the field by trainees.

The aggregated wound density information may be used by tactical military personnel to adapt training and/or protocol to better protect body areas that most commonly sustain surface wounds or most commonly sustain severe surface wounds.

The system 500 may be designed to enable the graphical representation and/or statistical analysis of the aggregated wound density information to be exported to other analytical packages.

Figure 5:
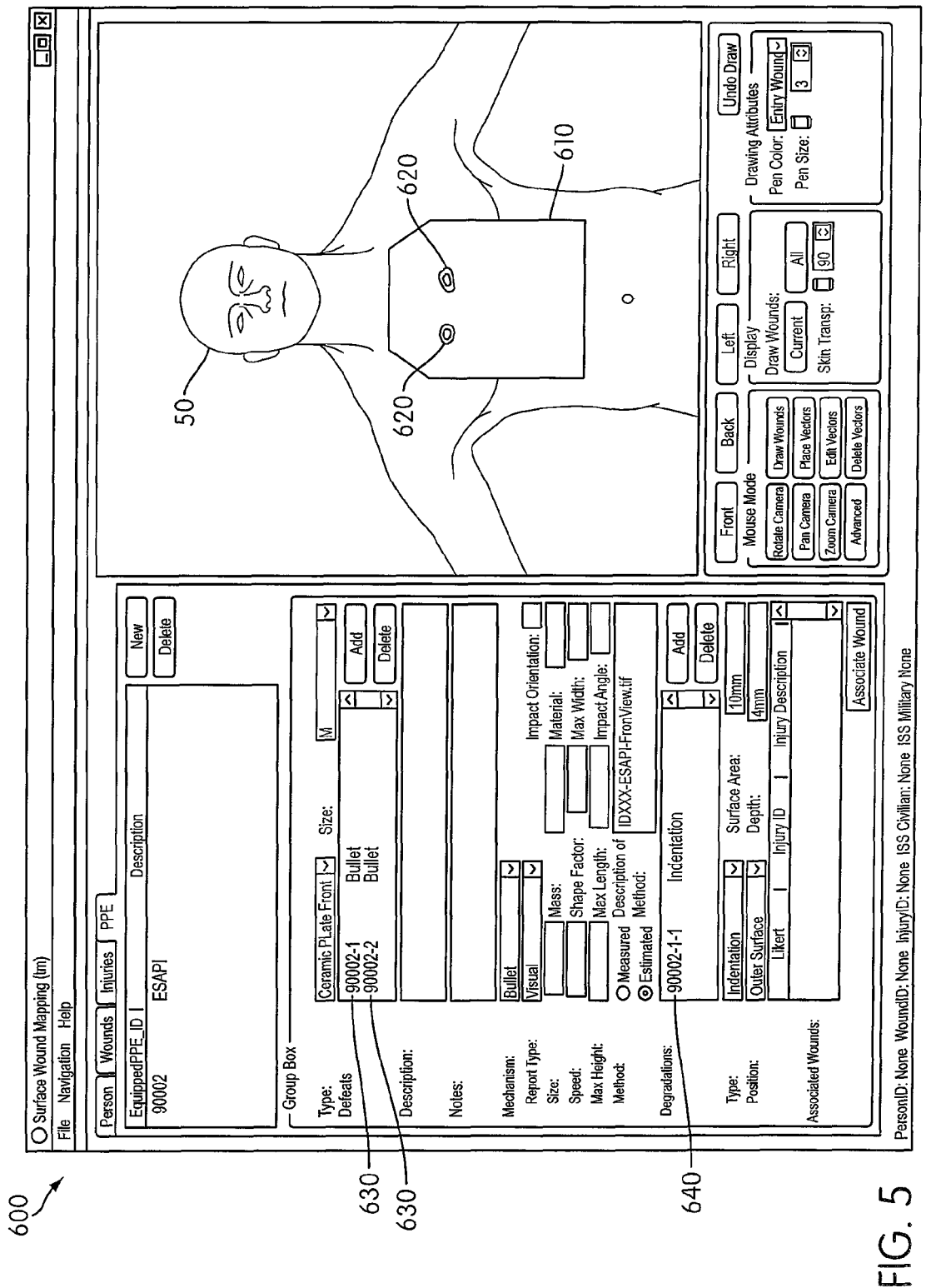
FIG. 5 is a screenshot illustrating the use of an associated data entry system for recording data about the protective devices that a subject human was utilizing at the time of wounding.

As shown in FIG. 5, the system 10 may also include a personal protective equipment (PPE) subrecord entry tool 600 to enable the examiner to enter data about any PPE 610 that the subject human was utilizing when wounded. The examiner may select the applicable PPE from a catalog of equipment previously entered into the system, e.g. SAPI (small arms protective insert) plate size medium.

Additionally and/or alternatively, the PPE subrecord entry tool 600 may enable the examiner to describe the nature of the PPE interactively. The interactive description provides a method for the examiner to describe the regions of the body that the PPE protects and the degree of protection that the PPE affords. The body region can either be from a predetermined list of regions, e.g. right leg, head, neck, or from a graphical markup (similar to the wound markup) on the 3D model 50 of the body. One method of describing the degree of protection is in terms of the threat type and the stopping power e.g. high velocity projectile and amount of energy absorption for PPE such as body armor, or fire and temperature/resistance duration for PPE such as fire retardant gear.

The PPE subrecord entry tool 600 may provide a method for describing the post-wounding condition 640 of the PPE 610. The computer-generated representation of the PPE 610 (e.g., 3D or 2D) can be displayed separate from, or in conjunction with, the model 50. This display can be used in the same manner as the wound drawing feature 80 to illustrate where the PPE 610 was damaged. The severity of the damage can be recorded (e.g. portion of the PPE 610 is missing, device is cracked, device is perforated, device is dented). Multiple instances of damage 620 can be noted as separate entries 630 within each PPE subrecord. A mechanism of damage, e.g. bullet, fire, can be noted for each instance of damage 630 that is recorded. 3D vector data may also be added to each entry 630 to describe the angle of incidence of an object causing the damage to the PPE 610. The vector data may be added to the subrecord in the same manner as vector data is added to the surface wound subrecord.

Information about damage to the PPE 610 may alternatively be entered without the interactive markup. In this case the system 600 provides a list of regions on the PPE 610 (e.g. front, back, side) to choose from in describing the part of the device that was damaged.

The PPE subrecord entry tool 600 may provide a method for linking information about wounds or injuries with information about damage to the PPE, similar to the above-described association of wound information to injury information. Thus if the subject human is shot and the bullet travels through a protective vest and then enters the subject human, the damage to the vest and the wound on the human or injuries sustained can be associated.

The PPE subrecord entry tool 600 may enable an examiner to enter additional information associated with the PPE 610 into the PPE subrecord. Such information may include any of the information described above with respect to the surface wound and/or injury subrecords (e.g., incident information (e.g., location, time, date, etc.), associated surface wound or injury information, vector information relating to the angle of incidence of an object that damaged the PPE 610, detailed information relating to the mechanism of damage to the PPE 610 (e.g., artillery (e.g., weapon caliber), type of explosive (e.g., land mine, IED), fire, etc.) other tactical incident information, etc.).

The PPE subrecord entry tool 600 may enable an examiner to qualitatively or quantitatively record a perceived PPE-caused reduction in extent of wound and/or severity of injury. Such information may be recorded for each damage subentry such that the benefit of the PPE is linked to a location on the PPE.

Placement of the PPE 610 relative to the model 50 can be adjusted interactively or can be adjusted via an automated registration process. Such automated registration process could use landmarks on the PPE 610 and landmarks on the model 50, or on the model 50 as marked up with wound information to perform the registration. In the case of the bullet shot described above the location of the damage in the vest and the entrance wound in the person may be included as associating landmarks.

The analysis system 500 may additionally and/or alternatively analyze aggregated PPE data captured via the PPE subrecord entry tool 600. The system 500 may be used to generate reports as to the protective coverage and wound information in graphical and non-graphical representations. The reports may describe wound and/or injury density and/or severity relative to protective coverage. The reports may be customized based on characteristics of the wound (e.g. location, type, causative factor, or by characteristics of the coverage, e.g. type of device, protection details, or by other related information as gathered by the system) or injury. The reports may be for an individual or a select collection of individuals (e.g., via record filtering based on the type of PPE used, the type of PPE failure, and/or any other information in the aggregated records).

The system 500 may aggregate PPE subrecords to identify damage density as a function of surface location on the PPE. Such damage density may be weighted based on the severity of the damage sustained. Hybrid densities that incorporate wound and/or injury information may also be generated. For example, if PPE damage is associated with wound and/or injury information, the density information may be weighted based on associated injury severity or wound information. Such weighted analysis may help PPE designers to better focus on areas of the PPE where damage is most frequent and/or causes the most severe injuries.

The system 500 may aggregate PPE subrecords for a particular type of PPE outside of the context of associated wounds and/or injuries. Such aggregation may be displayed as a damage density map on the surface of the 3D representation of the particular PPE. Severity of damage to the PPE may be weighted relative to damage location and damage volume over the aggregated records in creating the damage density map. Such aggregated data may be used to analyze weaknesses in PPE to improve design.

To facilitate quantitative analysis of the information in the subrecords, various qualitative information may be either initially recorded or subsequently converted into quantitative information that can be statistically analyzed. For example, with respect to the severity of damage to a PPE, the damage severity can be scored on a scale of 1 to 100 using standardized correlations between qualitative and quantitative severity (e.g., scratch=4; small dent=10, fracture=30, through-hole=90, part of PPE missing=90, etc.).

The system 500 may graphically display various combinations of aggregated information (e.g., wound density, PPE damage density, injury density, and/or weighted combinations of these and other aggregated information). The combinations of aggregated information may be overlaid on each other using different visualization mechanisms (e.g., different color combinations, variable vector/hedgehog illustrations, geographical distortion, etc.). Additionally and/or alternatively, the system 500 may enable the display to jump between different displayed information.

The system 500 may provide an ability to describe alternate configurations of protective gear than that actually worn at the time of wounding. The system 500 may further provide a method for assessing this alternate configuration relative to the wounds recorded and to predict if different wound characteristics would have resulted from the different protective configuration.

In addition to the above-described techniques for filtering database records for analysis, the system 500 may enable a user to filter the records based on specific wound (and/or damage) location. For example, the system 500 may enable a user to draw a surface region onto the model 50 (or a computer-generated model of a particular PPE) in the same manner as described above with respect to the identification of surface wounds (or PPE damage). The system 500 can then automatically filter the database records and analyze only the subset of records that contain surface wounds (or PPE damage) in the drawn surface region. Such a surface location filter can facilitate the analysis of specific body and/or PPE regions. The quantified location information generated by the system 500's surface region selection feature, the wound drawing feature 80, and the PPE damage drawing feature facilitate this location-specific filtering.

The foregoing description is included to illustrate the operation of the preferred embodiments and is not meant to limit the scope of the invention. To the contrary, those skilled in the art should appreciate that varieties may be constructed and employed without departing from the scope of the invention, aspects of which are recited by the claims appended hereto.

What is claimed is:

1. A method of collecting wound information, comprising:
receiving location information of a surface wound sustained by a first subject human, the location information comprising a size, shape, and location of the surface wound, said size, shape, and location being quantitatively defined relative to a 3D human model;
recording the location information onto a memory device;
recording injury information concerning an injury sustained by the first subject human onto the memory device;
recording onto the memory device a relationship between the location information and the injury information;
displaying on a display a computer-generated 3D human model comprising computer-generated skin; and
responsive to said receiving of said location information, drawing the location information including the size, shape, and location of the surface wound onto the displayed computer-generated skin of the computer-generated 3D human model,
wherein the received location information comprises an area of the surface wound,
wherein drawing the location information comprises drawing the area of the surface wound on the computer-generated skin of the computer-generated 3D human model,
wherein the computer-generated 3D human model comprises internal anatomical landmarks, and
wherein the method further comprises selectively changing a transparency of the skin to facilitate location of the surface wound relative to at least one of the internal landmarks.

2. The method of claim 1, wherein the internal landmarks comprise at least one of skeletal landmarks and internal organ landmarks.

3. A method of collecting wound information, comprising:
receiving location information of a surface wound sustained by a first subject human, the location information comprising a size, shape, and location of the surface wound, said size, shape, and location being quantitatively defined relative to a 3D human model;
recording the location information onto a memory device;
recording injury information concerning an injury sustained by the first subject human onto the memory device;
recording onto the memory device a relationship between the location information and the injury information;
display on a display a computer-generated 3D human model comprising computer-generated skin;
responsive to said receiving of said location information, drawing the location information including the size, shape, and location of the surface wound onto the displayed computer-generated skin of the computer-generated 3D human model; and
prior to said receiving of said location information, receiving a body characteristic for the first subject human, wherein a characteristic of the computer-generated 3D human model is based on the received body characteristic, and wherein the characteristic of the computer-generated 3D human model comprises a height, weight, gender, or body type,
wherein the 3D human model that the size, shape and location are quantitatively defined relative to is a standardized 3D human model such that the recorded location information is defined relative to a reference frame of the standardized 3D human model.

4. The method of claim 3, wherein:
the recorded surface wound location information comprises a first recorded surface wound location information;
the recorded injury information comprises a first recorded injury information;
the recorded relationship comprises a first recorded relationship;
the memory device comprises a plurality of additional recorded surface wound location informations of a respective plurality of surface wounds sustained by a respective plurality of additional subject humans, a plurality of additional recorded injury informations concerning a respective plurality of injuries sustained by the respective plurality of additional subject humans, and a plurality of additional recorded relationships between the respective location information and injury information of respective ones of the plurality of additional subject humans,
wherein a plurality, of said plurality of recorded surface wound location informations each comprise a size, shape, and location of the respective surface wound on the respective subject human, each such size, shape, and location being quantitatively defined relative to the reference frame of the standardized 3D human model.

5. The method of claim 4, further comprising comparing the first recorded surface wound location information to the plurality of additional recorded surface wound location informations.

6. The method of claim 4, further comprising aggregating the first recorded surface wound location information and the plurality of additional recorded surface wound location informations to identify wound density as a function of skin location on the standardized 3D human model.

7. A computer implemented method of collecting wound information, the method comprising:
storing in a memory device a plurality of surface wound location informations, each relating to a respective surface wound sustained by a respective subject human and comprising a size, shape, and location of the respective surface wound on the respective subject human;
aggregating the location informations from a plurality of the plurality of surface wound location informations; and
displaying onto a display device wound density of the aggregated location informations as a function of skin location on a computer-generated skin of the 3D human model,
wherein, prior to said aggregating, said size, shape, and location of said respective surface wounds of said plurality of said plurality of surface wound location informations are quantitatively defined relative to a common reference coordinate system of a 3D human model, and
wherein at least two of said plurality of the plurality of surface wound location informations relate to respective surface wounds sustained by different respective subject humans.

8. The method of claim 7, further comprising:
storing in the memory device a plurality of injury informations, each identifying a severity of a respective injury associated with a respective one of the surface wounds sustained by a respective one of the subject humans; and
storing in the memory respective relationships between respective ones of the injury informations and respective ones of the surface wound location informations,
wherein said displaying of wound density comprises displaying wound density as a function of the injury severity.

9. The method of claim 7, further comprising:
selecting a subset of the plurality of surface wound location informations, the subset being based on at least one selected criterion associated with the surface wound location informations,
wherein said aggregating comprises aggregating the surface wound location informations of the selected subset, and
wherein said displaying comprises displaying onto the display device wound density of the selected subset as a function of skin location on the computer-generated skin of the 3D human model.

10. The method of claim 9, further comprising:
storing in the memory device a plurality of injury informations, each relating to a respective injury associated with a respective one of the surface wounds sustained by a respective one of the subject humans;
storing in the memory device relationships between respective ones of the injury informations and respective ones of the surface wound location informations; and
selecting the subset based on whether the injury information associated with a respective surface wound location information satisfies the at least one selected criterion.

11. The method of claim 9, further comprising receiving a user's selection of what at least one criterion to use as the at least one selected criterion.

12. The method of claim 9, wherein the at least one selected criterion comprises: surface wounds occurring before or after selected times or dates;
surface wounds occurring during selected time or date ranges; AIS code of injuries or surface wounds; injury or surface wound severity; information associated with injuries that caused the surface wound; injury mechanism; geographic location where surface wound was incurred;
surface wound type; location of the surface wound on the subject human; subject human information; an ISS code for the subject human; a presence of personal protective equipment used by the subject human when the surface wound was sustained; or a type of personal protective equipment used by the subject human when the surface wound was sustained.

13. A system for collecting wound information, the system comprising a processor and a memory device, the processor being configured to:
store in the memory device a plurality of surface wound location informations, each relating to a respective surface wound sustained by a respective subject human and comprising a size, shape, and location of the respective surface wound on the respective subject human; and
aggregate the location informations from a plurality of the plurality of surface wound location informations,
wherein, prior to said aggregating, said size, shape, and location of said respective surface wounds of said plurality of said plurality of surface wound location informations are quantitatively defined relative to a common reference coordinate system of a 3D human model,
wherein at least two of said plurality of the plurality of surface wound location informations relate to respective surface wounds sustained by different respective subject humans, and
wherein the system further comprises a display device, wherein the processor is configured to display onto the display device wound density of the aggregated location informations as a function of skin location on a computer-generated skin of the 3D human model.

14. The system of claim 13, wherein the processor is configured to:
store in the memory device a plurality of injury informations, each injury information identifying a severity of a respective injury associated with a respective one of the surface wounds sustained by a respective one of the subject humans; and
store in the memory respective relationships between respective ones of the injury informations and respective ones of the surface wound location informations, and
display on the display device said wound density as a function of the injury severity.

15. The system of claim 13, wherein the processor is configured to:
select a subset of the plurality of surface wound location informations, the subset being based on at least one selected criterion associated with the surface wound location informations,
aggregate the surface wound location informations of the selected subset, and display onto the display device wound density of the selected subset as a function of skin location on the computer-generated skin of the 3D human model.

16. The system of claim 15, wherein the processor is configured to:
- store in the memory device a plurality of injury informations, each relating to a respective injury associated with a respective one of the surface wounds sustained by a respective one of the subject humans;
- store in the memory device relationships between respective ones of the injury informations and respective ones of the surface wound location informations; and
- select the subset based on whether the injury information associated with a respective surface wound location information satisfies the at least one selected criterion.

17. The system of claim 15, wherein the at least one selected criterion comprises: surface wounds occurring before or after selected times or dates;
- surface wounds occurring during selected time or date ranges; AIS code of injuries or surface wounds; injury or surface wound severity; information associated with injuries that caused the surface wound; injury mechanism; geographic location where surface wound was incurred;
- surface wound type; location of the surface wound on the subject human; subject human information; an ISS code for the subject human; a presence of personal protective equipment used by the subject human when the surface wound was sustained; or a type of personal protective equipment used by the subject human when the surface wound was sustained.

* * * * *